United States Patent
Lou et al.

(10) Patent No.: US 9,651,480 B2
(45) Date of Patent: May 16, 2017

(54) ONLINE DETECTION METHOD OF GASEOUS ALKALI METAL CONCENTRATION IN BOILER BURNING FLAME

(71) Applicant: HUAZHONG UNIVERSITY OF SCIENCE AND TECHNOLOGY, Wuhan, Hubei (CN)

(72) Inventors: Chun Lou, Hubei (CN); Yanfei Tian, Hubei (CN)

(73) Assignee: Huazhong University of Science and Technology, Wuhan, Hubei (CN)

( * ) Notice: Subject to any disclaimer, the term of this patent is extended or adjusted under 35 U.S.C. 154(b) by 0 days.

(21) Appl. No.: 15/104,427

(22) PCT Filed: Jun. 4, 2015

(86) PCT No.: PCT/CN2015/080739
§ 371 (c)(1),
(2) Date: Jun. 14, 2016

(87) PCT Pub. No.: WO2016/115804
PCT Pub. Date: Jul. 28, 2016

(65) Prior Publication Data
US 2016/0363528 A1    Dec. 15, 2016

(30) Foreign Application Priority Data
May 18, 2015    (CN) .......................... 2015 1 0253375

(51) Int. Cl.
G01J 3/30    (2006.01)
G01N 21/31    (2006.01)
(Continued)

(52) U.S. Cl.
CPC ............. *G01N 21/31* (2013.01); *G01N 21/72* (2013.01); *G01N 33/0036* (2013.01); *G01J 3/30* (2013.01)

(58) Field of Classification Search
CPC ........ G01N 21/31; G01N 21/72; G01N 21/71; G01N 33/00; G01N 1/22; G01N 30/68
See application file for complete search history.

(56) References Cited

U.S. PATENT DOCUMENTS 5,641,282 A    6/1997  Lee et al.
7,229,833 B1 *  6/2007  Andersson ............. G01N 21/33
                                                 422/83

FOREIGN PATENT DOCUMENTS

CN    101487740    7/2009
CN    101701850    5/2010
(Continued)

*Primary Examiner* — Abdullahi Nur
(74) *Attorney, Agent, or Firm* — Hamre, Schumann, Mueller & Larson, P.C.

(57) ABSTRACT

Provided is an online detection method of gaseous alkali metal concentration in boiler burning flame. The method includes selecting the user characteristic spectral line to be measured; based on the characteristic spectral line of the alkali metal, constructing a fitting model between radiation strength of the characteristic spectral line of the alkali metal in the burning flame and the gaseous alkali metal concentration and flame temperature; calibrating the spectrograph under absolute radiation strength; measuring a flame object corresponding to an alkali metal concentration by the calibrated spectrograph to obtain the radiation strength and flame temperature of the characteristic spectral line of the alkali metal. The detection method can detect the concentration of the gaseous alkali metal in the burning flame of the detection furnace quickly and accurately as well as detect the content of the base metals, involves simple devices, low cost, and is suitable for field measurement.

3 Claims, 3 Drawing Sheets

(51) Int. Cl.
 *G01N 33/00* (2006.01)
 *G01N 21/72* (2006.01)

(56) References Cited

FOREIGN PATENT DOCUMENTS

| | | |
|---|---|---|
| CN | 102053067 | 5/2011 |
| CN | 103091303 | 5/2013 |
| CN | 104062250 | 9/2014 |
| JP | H08166127 | 6/1996 |

* cited by examiner

ONLINE DETECTION METHOD OF GASEOUS ALKALI METAL CONCENTRATION IN BOILER BURNING FLAME

TECHNICAL FIELD

The invention relates to the field of detection of flame emitting spectrum, and particularly to an online detection method of gaseous alkali metal concentration in boiler burning flame.

BACKGROUND OF THE INVENTION

With the economic development, power consumption gradually increases, energy consumption significantly grows, and environment problem becomes increasingly prominent, the power plant must use new coal source and develop new burning methods to eliminate the pressure from both energy consumption and environment protection. In recent years, the coal having high base metal content is widely used, which results in hearth slag and heated area ash. Forest waste, agricultural waste, water plant, oil plant, processing wastes of organic matter, human and animal excreta and municipal solid waste are regarded as the regeneration energy with bright application prospect. Compared with common stone coal, the biomass fuel has higher alkali metal content and thus is easily gasified during the burning process, which often results in high temperature corrosion and the formation of scaled heating surface, furnace slag, etc. It is very important to measure the gaseous metal concentration in the burning flame for the safety operation of high base coal and biomass boiler; meanwhile, it is important to guide the research of the reliving mechanism and model setting of alkali metal.

The fiber optic spectrometer taking CCD array as the spectral measurement component can detect the spectral radiation information of the burning flame under different wavelengths. It can be known from National Institute of Standards and Technology (NIST) Atomic Spectra Database that the characteristic atomic emission spectrum of main alkali metal is: Li (670.776 nm, 670.791 nm), Na (588.995 nm, 589.592 nm), K (766.490 nm, 769.896 nm) and Rb (780.027 nm, 794.760 nm), all of which favors the qualitative and quantitative analysis of alkali metal. The traditional alkali metal detection method is offline detection, such as flame atomic absorption spectrometry, flame photometry, inductive coupling inductively coupled plasma atomic emission spectrometry, graphite furnace atomic absorption spectrometry, etc.; the methods need to carry out pre-treatment to the collected sample to achieve the test condition. It has complex operation; the offline detection method cannot obtain the gaseous alkali metal distribution rule in the burning process. Along the development of laser technology, the researcher can measure alkali metal Na, K contents of brown coal and pine wood by Laser-Induced Breakdown Spectroscopy (LIBS). However, with regard to large industrial furnace, LIBS online detection technology has obvious disadvantages such as complex equipment, complex operation and high cost. Although LIBS detection neglects the temperature change, the constant temperature must be maintained, and the measuring conditions are rigorous, which is unfavorable to the industrial generalization of LIBS.

SUMMARY OF THE INVENTION

In view of the above-mentioned problems, it is an objective of the invention to provide an online detection method of gaseous alkali metal concentration in boiler burning flame. According to the features of the burning flame in the boiler, the concentration of gaseous alkali metal in the boiler flame is detected by flame emission spectrum; the problem that the current detection method is difficult to be applied in the detection of the gaseous alkali metal concentration in large industrial boiler is solved; the detection method is simple and accurate, involves simple devices and low cost, and is suitable for the online detection of gaseous metal concentration in large industrial boiler.

In accordance with an aspect of the invention, provided is an online detection method of gaseous alkali metal concentration in boiler burning flame, comprising steps of:

(1) constructing a fitting model based on characteristic spectral line: selecting characteristic spectral line of an alkali metal to be measured; based on the characteristic spectral line of the alkali metal, constructing a fitting model between radiation strength $I_{Alkali}$ of the characteristic spectral line of the alkali metal in the burning flame and the gaseous alkali metal concentration $C_{Alkali}$ and flame temperature T:

$$I_{Alkali} = \sum_{0}^{m} \sum_{0}^{n} a_{mn}(C_{Alkali})^m T^n,$$

where $a_{mn}$ is a polynomial fitting coefficient; orders m, n are positive integers; T is a flame temperature of a measuring object; and the unit is K;

(2) calibrating: calibrating the spectrograph under absolute radiation strength; measuring a flame object of the known alkali metal concentration by the calibrated spectrograph to obtain the radiation strength and flame temperature of the characteristic spectral line of the alkali metal; introducing radiation strengths and flame temperatures corresponding to different alkali metal concentrations to the fitting model $$I_{Alkali} = \sum_{0}^{m} \sum_{0}^{n} a_{mn}(C_{Alkali})^m T^n$$

to obtain a specific value of the polynomial fitting coefficient $a_{mn}$; and (3) online detection: measuring a radiation spectrum of the boiler burning flame in real time by the calibrated spectrograph to obtain the radiation strength and the flame temperature corresponding to the characteristic spectral line of the alkali metal; introducing the radiation strength and the flame temperature corresponding to the characteristic spectral line of the alkali metal, and the specific value of the polynomial fitting coefficient $a_{mn}$ in step (2) to the fitting model constructed in step (1), to calculate an actual concentration of gaseous alkali metal in the boiler burning flame to realize the online detection of gaseous alkali metal concentration in the boiler burning flame.

Preferably, the construction of the fitting model $$I_{Alkali} = \sum_{0}^{m} \sum_{0}^{n} a_{mn}(C_{Alkali})^m T^n$$

is as follows:

(1.1) according to flame spectrometric analysis, atom or ion of an element absorbs energy of high temperature flame and is excited from the ground state; the distribution of the ground state atom $N_0$ and the excited state atom $N_i$ of unit volume meets the maxwell-boltzmann distribution rule in statistic mechanics, namely:

$$N_i = \frac{g_i}{g_0} \cdot N_0 \cdot e^{-\frac{E_i}{kT}}; \qquad (1)$$

where, $g_i$, $g_0$ are the statistical weights of the excited state and the ground state; $E_i$ is excited energy; k is a boltzmann constant; and T is excited temperature.

(1.2) relation between the spectral line intensity $I_{ij}$ generated by transition of energy levels i,j and the number of excited atom is as follows:

$$I_{ij} = N_i \cdot A_{ij} \cdot h \cdot v_{ij} \qquad (2)$$

where, $A_{ij}$ is the transition probability of two energy levels; h is a Planck constant; $v_{ij}$ is the frequency of emission line; and the formula (1) is substituted into the formula (2) to obtain the following formula:

$$I_{ij} = \frac{g_i}{g_0} \cdot A_{ij} \cdot h \cdot v_{ij} \cdot N_0 \cdot e^{-\frac{E_i}{kT}}; \qquad (3)$$

(1.3) based on formula (3), the radiation strength of atom characteristic spectral line is related to the ground atom number $N_0$ and excited temperature T; the ground atom number $N_0$ is related to the concentration; the radiation strength of atom characteristic spectral line $I_{Alkali}$ s represented by a function of alkali metal concentration $C_{Alkali}$ and flame temperature T; and the fitting model is obtained by minimum square law:

$$I_{Alkali} = \sum_{0}^{m} \sum_{0}^{n} a_{mn}(C_{Alkali})^m T^n.$$

Preferably, the spectrograph is calibrated on a blackbody furnace.

Generally speaking, compared with the current technology, the above technical scheme has the following technical advantages:

1. Based on the emission spectrum analysis in the visible light range of the alkali metal flame, the fitting model between the characteristic spectral line of the alkali metal, the gaseous alkali metal concentration, and the flame temperature in the flame is constructed; thus, a simple and effective detection method of gaseous alkali metal concentration in the burning flame is established, so as to obtain the distribution rule of the gaseous alkali metal in the furnace; it is of great significance to prevent and analyze the alkali metal corrosion and slag; and the invention is a non-contracting measuring method, so it has no interface on the flame object.

2. The detection method in the invention can detect the concentration of the gaseous alkali metal in the burning flame of the detection furnace quickly and accurately as well as detect the content of the base metals; it involves simple devices, low cost, and is suitable for field measurement; it can be directly applied to detect the gaseous alkali metal concentration in large industrial boiler and realize the online measurement of gaseous alkali metal concentration in the burning process of alkali metal fuel.

BRIEF SPECIFICATION OF THE DRAWING

EMBODIMENTS OF THE INVENTION

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Figure 1:
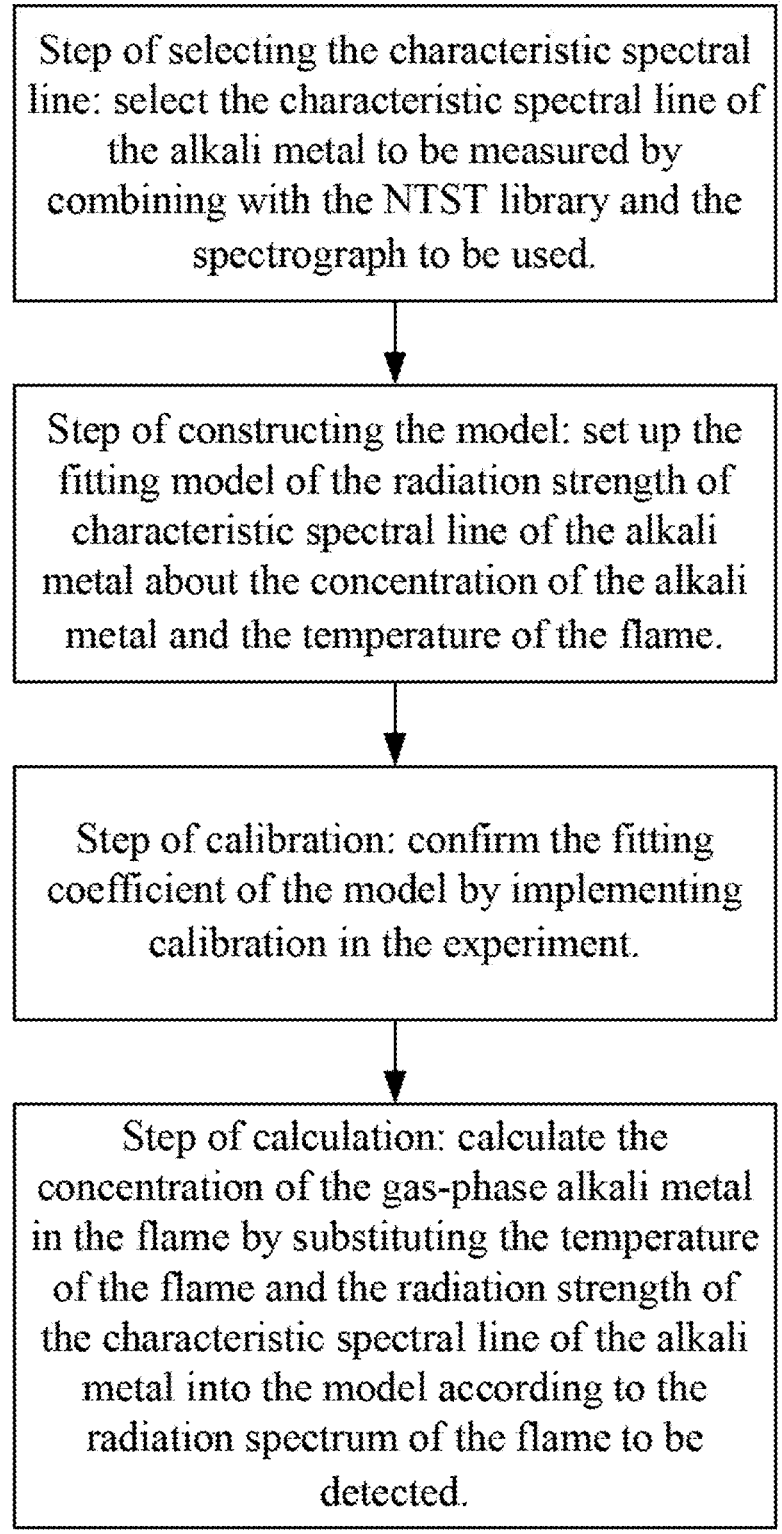
FIG. 1 is a flowchart of an online detection method of gaseous alkali metal concentration in boiler burning flame of the invention.

The flow block diagram is shown in FIG. 1; and the on-line detection method of concentration of the gas-phase alkali metal in the combustion flame shall include following steps:

(1) Selection of Characteristic Spectral Line and Construction of the Fitting Model The elements are in the ground state in the normal state and are activated in the excited state (upper state) when the atom or ion of the element absorbs the energy in the high-temperature flame; a series of characteristic spectral lines are emitted because the excited state is extremely unstable, are subjected to transition into the lower state or the ground state and release the excessive energy at the same time. The spectral line emitted in the ground state after being returned to the lowest excited state is called the first resonance line which is the strongest spectral lines and the most sensitive spectral line during analysis of element. From the NIST Atomic Spectra Database, each alkali metal shall have its own atom characteristic spectral line, and the characteristic spectral lines having stronger strength in the first resonance line are Li (670.776 nm, 670.791 nm), Na (588.995 nm, 589.592 nm), K (766.490 nm, 769.896 nm) and Rb (780.027 nm, 794.760 nm) respectively, which are the characteristic spectral lines of the alkali metals to be selected in the theory. Moreover, the smallest wavelength that the spectrograph can distinguish is taken into account when selecting the characteristic spectral line because of different resolutions of the spectrographs during actual measurement.

The AvaSpec-2048-USB2 spectrograph is applied to measure the radiation spectrum of the flame in the garbage incinerator; and the atom characteristic spectral lines of the alkali metal detected actually are Li (670.451 nm), Na (589.139 nm), K (766.538 nm, 769.886 nm) and Rb (779.920 nm, 794.388 nm) respectively because the resolution of the spectrograph is 0.8 nm, and the spectral lines of Na (589.139 nm), K (766.538 nm, 769.886 nm) are the most obvious.

All characteristic spectral lines detected can be applied to quantitative measurement theoretically; however, the characteristic spectral lines of elements K and Rb are kept away from its interference as far as possible because the characteristic spectral lines may occur to Ar at the places 772.376 nm and 772.421 nm in view of interference from the characteristic spectral lines of other elements. Therefore, Li (670.451 nm), Na (589.139 nm), K (766.538 nm) and Rb (794.388 nm) are selected in allusion to the characteristic spectral line of the alkali metal of the invention.

The fitting model of the radiation strength $I_{Alkali}$ of the characteristic spectral line of the alkali metal in the flame about the concentration $C_{Alkali}$ of the gas-phase alkali metal and the temperature T of the flame are set up on the basis of the characteristic spectral lines selected.

(1.1) The ground state is changed as the excited state because the atom or ion of the element absorbs the energy in the high-temperature flame in thermodynamic equilibrium according to the spectral analysis of the flame; and the distributions of number of the ground state atoms $N_0$ and the number of the excited state atom $N_i$ within the unit volume shall meet the Maxwell-Boltzmann Distribution Law in the Statistical Mechanics, that is, $$N_i = \frac{g_i}{g_0} \cdot N_0 \cdot e^{-\frac{E_i}{kT}} \quad (1)$$

where $g_i$ and $g_0$ are the statistical weights of the excited state and the ground state, respectively; $E_i$ indicates the excited energy; k indicates the A boltzmann constant; and T indicates the excited temperature.

(1.2) While the spectral strength $I_{ij}$ generated during transition among two energy levels i and j is in direct proportion to the number of the excited atoms, that is, $$I_{ij} = N_i \cdot A_{ij} \cdot h \cdot v_{ij} \quad (2)$$

where h indicates the planck constant; $A_{ij}$ indicates the transition probability among two energy levels; $v_{ij}$ indicates the frequency of the emission spectral line; and the formula $$I_{ij} = \frac{g_i}{g_0} \cdot A_{ij} \cdot h \cdot v_{ij} \cdot N_0 \cdot e^{-\frac{E_i}{kT}} \quad (3)$$

can be acquired when the Formula (1) is substituted into the Formula (2).

(1.3) The radiation strength of the atom characteristic spectral line is related to the number $N_0$ of the atoms in the ground state and the excited temperature T from the Formula (3); while the number $N_0$ of the atoms in the ground state is related to the concentration; therefore, the function of the concentration of the $C_{alkali}$ metal and the flame temperature T can be applied to expression of radiation strength $I_{Alkali}$ of the characteristic spectral line of the alkali metal, and the binary polynomial function in Formula (4) can be acquired after fitting by using the least square method:

$$I_{Alkali} = \sum_0^m \sum_0^n a_{mn}(C_{Alkali})^m T^n, \quad (4)$$

where the $\alpha_{mn}$ indicates the fitting coefficient of the polynomial; the orders m and n are selected according to need as long as the fitting error is small enough (1%-5%). Moreover, the binary polynomial function is fitting model constructed.

In this embodiment, the greatest values of the orders m and n are 4, and the fitting relation $$\begin{aligned} I_{Alkali} = & a_{00} + a_{01} * T + a_{02} * T^2 + a_{03} * T^3 + a_{04} * T^4 + \\ & a_{10} * C_{Alkali} + a_{11} * C_{Alkali} * T + a_{12} * C_{Alkali} * T^2 + \\ & a_{13} * C_{Alkali} * T^3 + a_{20} * C_{Alkali}^2 + a_{21} * C_{Alkali}^2 * T + \\ & a_{22} * C_{Alkali}^2 * T^2 + a_{30} * C_{Alkali}^3 + a_{31} * C_{Alkali}^3 * T + a_{40} * C_{Alkali}^4 \end{aligned} \quad (5)$$

can be acquired when the above-mentioned values are substituted into the Formula (4), where the unit of the radiation strength $I_{Alkali}$ of the characteristic spectral line of the alkali metal is $W/m^3/sr$; the unit of the temperature T is K; and the concentration $C_{Alkali}$ of the gas-phase alkali metal is in ppm.

(2) Calibration

The collimating lens are installed on one end of the fiber detector in order to ensure the signals entering into the optical fiber and received by the spectrograph are from the flame radiation signals in the accumulated direction of the sight line at the measuring position; the original output signal of the spectrograph is one voltage after photovoltaic conversion, which cannot reflect corresponding radiation energy; the spectrograph system is subjected to calibration on the blackbody furnace in order to acquire the absolute radiation strength of the spectrum. The flame object of the concentration of the alkali metal known is measured by using the spectrograph system subjected to the absolute calibration of radiation strength in order to acquire the radiation strength of the characteristic spectral line of the alkali metal and the flame temperature. Moreover, the polynomial fitting coefficient $\alpha_{mn}$ of the model can be acquired by using calibration in the experiment and substituting the radiation strengths of the characteristic spectral lines and the flame temperatures corresponding to a series of different concentrations measured of alkali metal into the Formula (5).

Figure 2:
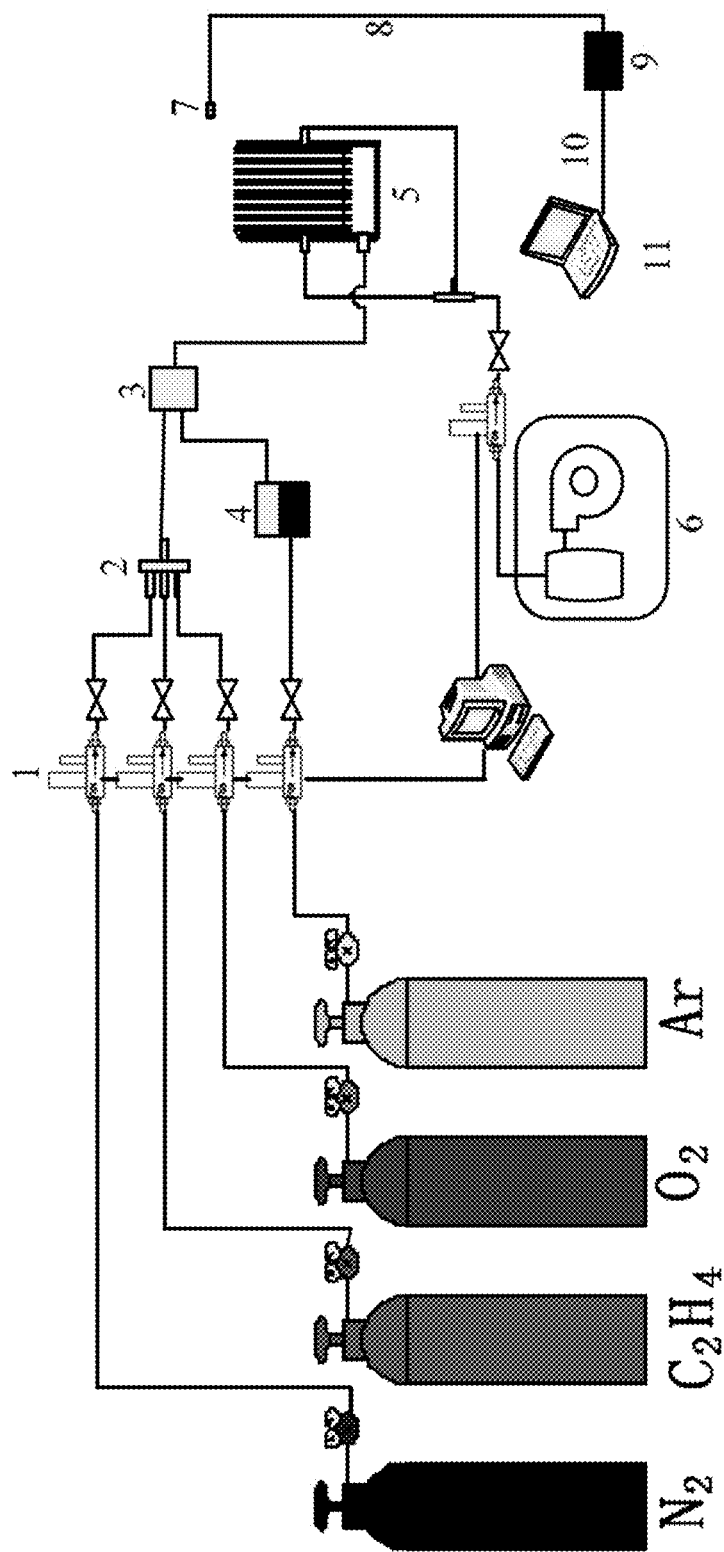
FIG. 2 is a diagram illustrating an experimental calibration system.

The polynomial fitting coefficient $\alpha_{mn}$ of the model is determined on the experimental calibration system which includes the laminar premixed flame multi jet burner, the fuel and oxidant feed device, the air feed device, the mass flow controller, the spectrum detection system, etc. mainly, as shown in the FIG. 2. Ethylene, oxygen and nitrogen shall enter into the mass flow controller 1 after being subjected to pressure adjustment by using the pressure regulating valve upon flowing out from the steel bottles and enter to the gas mixer 3 by using the four-way valves 2; the argon shall pass through the pressure regulating valve and the mass flow meter orderly after flowing out from the steel bottle; the vaporous alkali metal salt solution generated in the atomizer 4 with ultrasonic wave shall enter into the gas mixer 3; four gases shall enter into the jetting pipeline of the burner 5 after being mixed with the vaporous alkali metal salt solution uniformly. The wake airflow is supplied by using the air compressor 6 and enter into the mass flow controller and the wake airflow pipeline of the jetting burner 5 finally. The spectrum detection system is composed of the collimating lens 7, the optical fiber 8, the spectrogram 9, the USB connecting wire 10 and the notebook computer 11. Moreover, the specific working condition of the experimental calibration is shown in the following Table 1.

TABLE 1

| | | | | | Experimental environment | |
|---|---|---|---|---|---|---|
| Working condition | Flow of jet (L/min) | | | | Equivalent ratio | Wake flow (L/min) Air |
| | $C_2H_4$ | $O_2$ | $N_2$ | Ar | | |
| 1 | 1.0 | 3.75 | 2.95 | 0.8 | 0.8 | 4.0 |
| 2 | 1.0 | 3.33 | 3.37 | 0.8 | 0.9 | 4.0 |
| 3 | 1.0 | 3.0 | 3.7 | 0.8 | 1.0 | 4.0 |
| 4 | 1.0 | 2.73 | 3.97 | 0.8 | 1.1 | 4.0 |
| 5 | 1.0 | 2.5 | 4.2 | 0.8 | 1.2 | 4.0 |

The experiment is implemented specifically as follows:

(2.1) Calculation of concentration $C_{Alkali}$ of the gas-phase alkali metal and the radiation strength $I_{Alkali}$ of the characteristic spectral line of the alkali metal:

Acquire the concentrations $C_{Alkali}$ the gas-phase alkali metal in a series of flames (0 ppm, 2 ppm, 4 ppm, 6 ppm, 8 ppm and 10 ppm) and corresponding radiation strength $I_{Alkali}$ of the characteristic spectral line of the alkali metal by keeping the fluxes of the flue and the oxidant constant, that is, maintaining one constant temperature of the flame under one working condition and changing the concentration $C_s$ of the alkali metal solution.

In terms of calculation of the concentration of the alkali metal in the gas phase, the distribution of the alkali metal in the flame can be supposed to be uniform because the atomized alkali metal solution enters into the jetting tube after be blended with the fuel gas completely. The mass flow rate $v_m$ (g/s) of the solute of the alkali metal solution can be acquired after calculation by using the Formula (6):

$$v_m = C_s \cdot v_s \qquad (6)$$

where the $C_s$ indicates the concentration (%) of the alkali metal solution; $v_s$ indicates the consumption rate (g/s) of the alkali metal solution and can be acquired after statistical averaging by making the atomizer work for a long time.

The molar flow rate $v_{ms}$ (mol/s) of the alkali metal in the flame can be acquired after calculation by using the Formula (7):

$$v_{ms} = a_m \cdot v_m / M = \frac{a_m \cdot C_s \cdot v_s}{M}, \qquad (7)$$

where $\alpha_m$ indicates the mole fraction (%) of the alkali metal; and M indicates the molar mass (g/mol) of the alkali metal.

The total gas flow rate $v_f$ (L/s) in the flame region can be indicated by using $$v_f = (v_{O_2} + v_{N_2} + v_{C_2H_4}) \cdot T_f / T_r \qquad (8)$$

where $v_{O_2}$, $v_{N_2}$ and $v_{C_2H_4}$ indicate the volume flow rates of the oxygen, the nitrogen, the ethylene and can be acquired under the control of the flow controller; $T_f$ indicate the average temperature K of the flame; $T_r$ indicate the temperature K of the experimental room.

According to the state equation of the ideal gas, the molar flow rate $v_{mf}$ (mol/s) of the total gas in the flame area can be indicated by $$v_{mf} = \frac{P \cdot v_f}{R \cdot T_f} \qquad (9)$$

where R indicates the constant of the ideal gas; P indicates the pressure.

The Formula (10):

$$v_{mf} = \frac{P \cdot (v_{O_2} + v_{N_2} + v_{C_2H_4})}{R \cdot T_r} \qquad (10)$$

can be acquired after substituting the Formula (8) into the Formula (9) and simplifying them.

The volume concentration $C_{Alkali}$ (ppm) of the gas-phase alkali metal of the flame area can be acquired:

$$C_{Alkali} = v_{ms}/v_{mf} = \frac{a_m \cdot C_s \cdot v_s}{M} \cdot \frac{R \cdot T_r}{P \cdot (v_{O_2} + v_{N_2} + v_{C_2H_4})} \qquad (11)$$

after dividing the Formula (10) from the Formula (7).

Therefore, the volume concentration of the gas-phase alkali metal in the flame can be acquired after calculation by using the Formula (11) on the premise that the concentration of the alkali metal solution, the flow rate of the gas has been set and the room temperature is known in advance.

Then the radiation strength $I_{Alkali}$ of the characteristic spectral line of the alkali metal under the different flame temperatures can be measured from the spectrograph calibrated by changing the working condition, that is creating the environment at different temperatures and repeating the above-mentioned processes.

(2.2) Calculation of the temperature of the flame

As for calculation of the temperature of the flame, temperature $T_\lambda$ of the flame can be calculated after selecting two wavelengths $\lambda$ and $\lambda+\Delta\lambda$ with interval of $\Delta\lambda$ for the absolute radiation strength $I_d(\lambda)$ calibrated by the blackbody furnace with help of thermal radiation law:

$$T_\lambda = -C_2 \left( \frac{1}{\lambda} - \frac{1}{\lambda + \Delta\lambda} \right) / \ln \left( \frac{I_d(\lambda)}{I_d(\lambda + \Delta\lambda)} \frac{\lambda^5}{(\lambda + \Delta\lambda)^5} \right), \qquad (12)$$

where the Planck constant is $C_2=1.4388$ E$-2$, $I_d(\lambda)$ and $I_d(\lambda+\Delta\lambda)$ indicate the radiation strengths of the spectrums with wavelengths $\lambda$ and $\lambda+\Delta\lambda$ respectively.

(2.3) Calculation of fitting coefficient $\alpha_{mn}$:

The fitting coefficient $\alpha_{mn}$ can be calculated by substituting the different temperatures of flame under five experimental working conditions in the Table 1, different concentrations of the gas-phase alkali metal and corresponding radiation strengths of the characteristic spectral line of the alkali metal into the fitting relation set up in the Formula (5); therefore, the function model of the radiation strengths of the characteristic spectral line of the alkali metal about the concentration of the gas-phase alkali metal and the temperature of the flame can be confirmed.

(3) On-line detection

The radiation spectrum of the combustion flame in the furnace is measured by using the spectrograph calibrated, and the temperature of the flame can be calculated by using the thermal radiation law; and the concentration of the gas-phase alkali metal in the combustion flame can be acquired by extracting the radiation strengths of the characteristic spectral line of the alkali metal to be measured in the flame radiation spectrum and substituting the flame temperature to be calculated and the radiation strengths of the characteristic spectral line into the Formula (5) of the fitting coefficient known.

Figure 3:
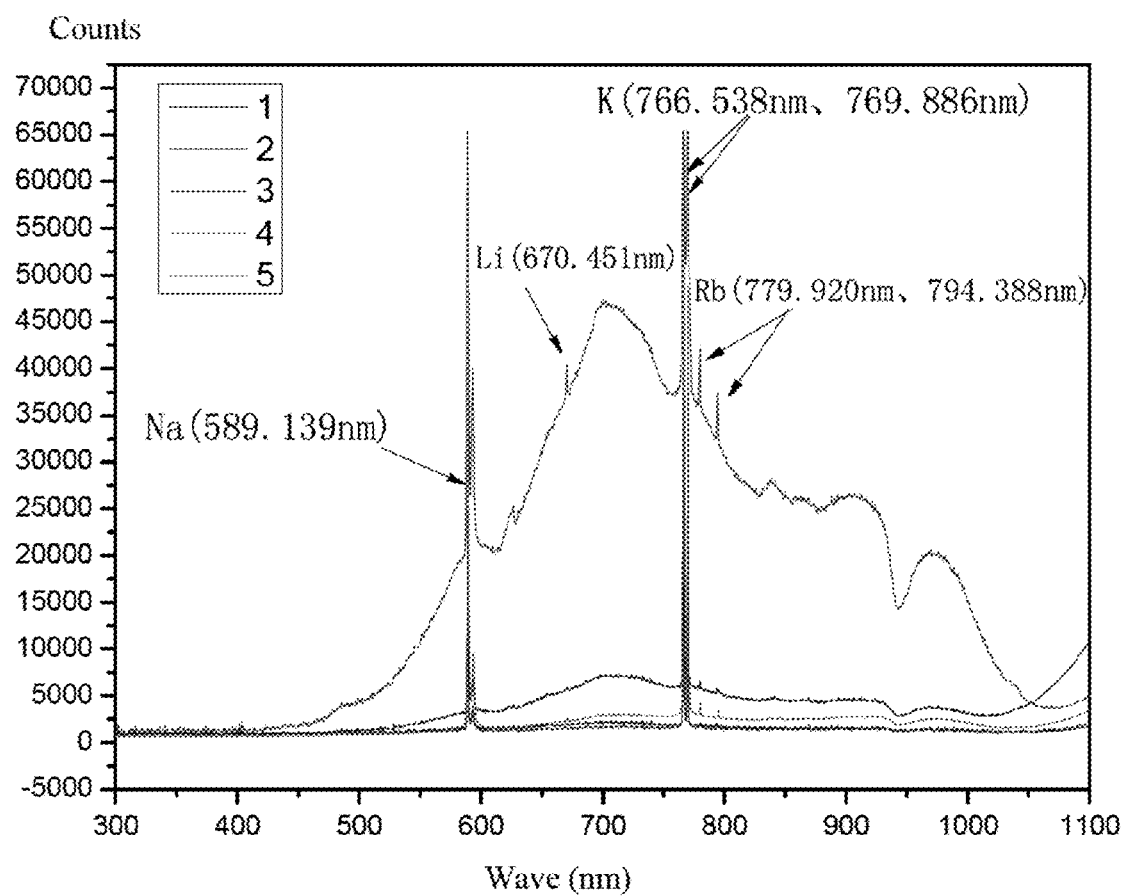
FIG. 3 is an emission line of the flame generated in waste burning in the visible light wave band.

The flame radiation spectrum diagram detected on the garbage incineration boiler by using the AvaSpec-2048-USB2 portable spectrograph is shown in the FIG. 3.

The spectrum detector is featured with CCD array of 2048 pixel, wavelength to be measured of 200-1100 nm, resolution of 0.8 nm, and signal to noise ratio of 200:1; the temperature T of the flame can be calculated by using the flame radiation spectrum acquired after actual measurement in the furnace; then the specific concentration of the gas-phase alkali metal in the flame to be measured can be acquired by substituting the radiation strength $I_{Alkali}$ of the characteristic spectral line of the alkali metal to be measured and the temperature T of the flame into the Formula (5) of the fitting coefficient $\alpha_{mn}$.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An online detection method of gaseous alkali metal concentration in boiler burning flame, the method comprising steps of:
   (1) constructing a fitting model based on characteristic spectral line: selecting characteristic spectral line of an alkali metal to be measured; based on the characteristic spectral line of the alkali metal, constructing a fitting model between radiation strength $I_{Alkali}$ of the characteristic spectral line of the alkali metal in the burning flame and the gaseous alkali metal concentration $C_{Alkali}$ and flame temperature T:

$$I_{Alkali} = \sum_0^m \sum_0^n a_{mn}(C_{Alkali})^m T^n,$$

where $\alpha_{mn}$ is a polynomial fitting coefficient; orders m, n are positive integers; T is a flame temperature of a measuring object, and the unit thereof is K;
   (2) calibrating: calibrating a spectrograph under absolute radiation strength; measuring a flame object corresponding to an alkali metal concentration by the calibrated spectrograph to obtain the radiation strength and flame temperature of the characteristic spectral line of the alkali metal; introducing radiation strengths and flame temperatures corresponding to different alkali metal concentrations to the fitting model $$I_{Alkali} = \sum_0^m \sum_0^n a_{mn}(C_{Alkali})^m T^n$$

to obtain a specific value of the polynomial fitting coefficient $\alpha_{mn}$; and
   (3) online detection: measuring a radiation spectrum of the boiler burning flame in real time by the calibrated spectrograph to obtain the radiation strength and the flame temperature corresponding to the characteristic spectral line of the alkali metal; introducing the radiation strength and the flame temperature corresponding to the characteristic spectral line of the alkali metal, and the specific value of the polynomial fitting coefficient $\alpha_{mn}$ in step (2) to the fitting model constructed in step (1), to calculate an actual concentration of gaseous alkali metal in the boiler burning flame to realize the online detection of gaseous alkali metal concentration in the boiler burning flame.

2. The method of claim 1, wherein the construction of the fitting model $$I_{Alkali} = \sum_0^m \sum_0^n a_{mn}(C_{Alkali})^m T^n$$

is as follows:
   (1.1) according to flame spectrometric analysis, atom or ion of an element absorbs energy of high temperature flame and is excited from the ground state; the distribution of the ground state atom $N_0$ and the excited state atom $N_i$ of unit volume meets the maxwell-boltzmann distribution rule in statistic mechanics, namely:

$$N_i = \frac{g_i}{g_0} \cdot N_0 \cdot e^{-\frac{E_i}{kT}}; \quad (1)$$

where, $g_i$, $g_0$ are the statistical weights of the excited state and the ground state; $E_i$ is excited energy; k is a boltzmann constant; and T is excited temperature;
   (1.2) relation between the spectral line intensity $I_{ij}$ generated by transition of energy levels i,j and the number of excited atom is as follows:

$$I_{ij} = N_i \cdot A_{ij} \cdot h \cdot v_{ij} \quad (2);$$

where, $A_{ij}$ the transition probability of two energy levels; h is a Planck constant; $v_{ij}$ is the frequency of emission line; and the formula (1) is substituted into the formula (2) to obtain the following formula:

$$I_{ij} = \frac{g_i}{g_0} \cdot A_{ij} \cdot h \cdot v_{ij} \cdot N_0 \cdot e^{-\frac{E_i}{kT}}; \quad (3)$$

based on formula (3), the radiation strength of atom characteristic spectral line is related to the ground atom number $N_0$ and the excited temperature T; the ground atom number $N_0$ is related to the concentration; the radiation strength of atom characteristic spectral line $I_{Alkali}$ is represented by a function of alkali metal concentration $C_{Alkali}$ and flame temperature T; and the fitting model is obtained by minimum square law:

$$I_{Alkali} = \sum_0^m \sum_0^n a_{mn}(C_{Alkali})^m T^n.$$

3. The method of claim 1, wherein the spectrograph is calibrated on a blackbody furnace.

* * * * *